United States Patent [19]

Bayerlein et al.

[11] Patent Number: 4,826,700

[45] Date of Patent: May 2, 1989

[54] GELLING AGENTS AND THICKENERS BASED ON CASSIA-GALACTOMANNANS

[75] Inventors: Friedrich Bayerlein, Krailling; Manfred Kuhn, München, both of Fed. Rep. of Germany; Michel Maton, Vaucresson, France

[73] Assignee: Diamalt Aktiengesellschaft, Munich, Fed. Rep. of Germany

[21] Appl. No.: 935,835

[22] Filed: Nov. 28, 1986

Related U.S. Application Data

[62] Division of Ser. No. 650,186, Sep. 13, 1984, Pat. No. 4,661,475.

[30] Foreign Application Priority Data

Sep. 30, 1983 [DE] Fed. Rep. of Germany ....... 3335593

[51] Int. Cl.$^4$ ................................................. A23L 1/04
[52] U.S. Cl. .................................. 426/573; 252/315.3; 252/8.51; 514/54
[58] Field of Search ......................... 426/573; 517/54; 252/315.3, 8.51

[56] References Cited

U.S. PATENT DOCUMENTS

| | | | |
|---|---|---|---|
| 3,740,388 | 6/1973 | Montgomery et al. | 260/209 R |
| 3,870,600 | 3/1975 | Youssef | 195/81 |
| 3,879,890 | 4/1975 | Chen et al. | 47/1.4 |
| 3,992,554 | 11/1976 | Blake et al. | 426/557 |
| 4,369,125 | 1/1983 | Kragen et al. | 252/315.3 |
| 4,453,979 | 6/1984 | DeMasi et al. | 106/188 |
| 4,647,470 | 3/1987 | Sanderson et al. | 426/573 |
| 4,746,528 | 5/1988 | Prest et al. | 426/573 |

FOREIGN PATENT DOCUMENTS 750382 1/1967 Canada .
A121707 9/1975 German Democratic Rep. .

OTHER PUBLICATIONS

Kapoor et al., Chem. Abs., 70, Abs. #75072d (1969).
Gupta et al., Chem. Abs., 80, Abs. #117426m (1974).
Lal et al., Chem. Abs., 78, Abs. #16383y (1973).
Patent Abstracts of Japan, vol. 7, No. 201, Sep. 6, 1983, p. C-184 (1346).

Primary Examiner—Edward A. Miller
Attorney, Agent, or Firm—Robbins & Laramie

[57] ABSTRACT

The invention relates to gelling agents and thickeners based on Cassia-galactomannans and especially a synergistic mixture of (a) Cassia-toragalactomannan, and (b) carrageenan, agar and/or xanthan.

16 Claims, No Drawings

GELLING AGENTS AND THICKENERS BASED ON CASSIA-GALACTOMANNANS

This is a continuation, division, of application Ser. No. 650,186, filed Sept. 13, 1984, now U.S. Pat. No. 4,661,475.

Gelling agents and thickeners are understood to be substances which are added during the process of manufacture and use to, for example, water or aqueous treatment fluids or solid or liquid foodstuffs or animal feeds, in order to achieve the desired consistency or viscosity. Virtually all conventional gelling agents and thickeners, with the exception of gelatin, are derivatives of polysaccharides, i.e., high-polymeric carbohydrates.

Polysaccharides are water-soluble or strongly swellable substances, so-called hydrocolloids, which in aqueous systems give colloidal, more or less highly viscous solutions or dispersions having plastic or pseudo-plastic flow. From this are derived the functional properties desired in the present case, such as a thickening action, water-binding capacity, stabilization of suspensions and emulsions in polyphase systems, and gel formation.

Galactomannans are, like the starches, vegetable reserve polysaccharides which occur in the endosperm cells of numerous seeds of *Leguminosae*. Upon germination of the seeds, they undergo enzymatic degradation and serve as nutrients for the seedling. The collective term "galactomannan" or "polygalactomannan" comprises all polysaccharides which are built up of galactose and/or mannose residues and in addition can also contain minor amounts of other sugar residues. There is a relatively large number of galactomannans, depending on their origin. The materials principally occur in the endosperm portions and seeds of various *Leguminosae* (legumes) such as guar, locust bean, tara, honey bean, flame tree, sesbania and species of Cassia. Galactomannans are built up of a linear mannose chain which itself is built up of mannopyranose rings linked by $\beta$-(1,4-glucoside bonds. To these rings are attached, as branches, isolated galactopyranose residues by $\alpha$-(1,6-glucoside bonds.

Among the numerous known galactomannans, three in particular have been isolated and used:

1. *Locust bean gum* (carubin) has long been known. It is obtained from the seeds of the locust bean tree (*Ceratonia siliqua* L.), which is a native of Mediterranean countries.

2. *Guar gum* (Guaran) is today the most important galactomannan. It is isolated from the seeds of the guar bean *Cyamopsis tetragonolobus* L. taub.) which is a native of India and Pakistan.

3. *Tara gum has only in recent times been produced in small amounts from the seeds of the tara tree (Cesalipinia spinosa)*, which grows particularly in Peru.

Carrageenans and agar are extracts of red algae and belong chemically to the group of the galactans. However, unlike cellulose and starch, they do not exhibit merely one type of 1,4-glycoside bond. The red algae galactomannans instead have alternate $\alpha$-1,3-bonds and $\beta$-1,4-bonds, and are therefore characterized as an a-b-a type of polysaccharide. Carrageenan is chemically not a homogeneous product but comprises the product group of sulfated galactans, with a proportion of the galactopyranose residues being present as a 3,6-anhydrogalactose residue. Certain fractions of carrageenans can be isolated from red algae extracts which are chemically defined with respect to their structure and are designated by Greek letters. Only lambda-, iota- and kappa-carrageenan are of commercial importance. Their different properties are principally explicable in terms of differences in the content of anhydrogalactose and sulfate ester groups. The 3,6-anhydrogalactose ring makes the galactans more strongly hydrophobic, i.e., the water solubility diminishes.

On the other hand, the sulfate group imparts more hydrophilic properties to the galactans, i.e., the water solubility increases. Moreoever, the presence of the sulfate groups has the consequence that the properties of carrageenan as an anionic polysaccharide can be modified by the presence of cations in the aqueous system. Thus, the gelling properties of kappa-carrageenan are greatly influenced by potassium ions and those of iota-carrageenan by calcium ions.

On the other hand, in agar, an electrically neutral galactan having a high anhydrogalactose content, gelling takes place independently of cations. Kappa-carrageenan has the highest anhydrogalactose content and the lowest sulfate content among the carrageenans, and as a result has the most powerful gel-forming properties. As already mentioned, it has a high dependence on the potassium ion concentration.

Lambda-carrageenan, on the other hand, does not contain any anhydrogalactose and has the highest sulfate ester content among the carrageenans. This has the consequence that it can no longer be caused to gel. A formula with the idealized structure of kappa-carrageenan is to be found in Robert L. Davidson's "Handbook of Water-Soluble Gums and Resins", FIG. 5.2, McGraw-Hill Book Company (1980).

Xanthan is a high-molecular-weight polysaccharide which is obtained in a fermentation process employing a microorganism *Xanthomonas campestris*. The main chain of xanthan has a cellulose structure. It consists of D-glucose units with $\beta$-1,4-bonds. The trisaccharide side-chains consist of two mannose units and one glucuronic acid unit. The terminal $\beta$-D-mannose unit is linked by a glycoside bond to the 4-position of the $\beta$-D-glucuronic acid, which in turn is linked by a glycoside bond to the 2-position of $\alpha$-D-mannose. This side-chain is linked to the 3-position of every second glucose residue of the polymer main chain. Roughly half the terminal D-mannose residues bear a pyruvic acid radical which is linked by a ketal bond to the 4- and 6-positions of the mannose ring. The non-terminal D-mannose unit of the side chain carries an acetyl group in the 6-position. The glucuronic acid group is present as a mixed potassium, sodium and calcium salt. A portion of the xanthan polymer chain is shown in Robert L. Davidson's "Handbook of Water-Soluble Gums and Resins", FIG. 24.1, McGraw-Hill Book Company (1980).

Although carrageenan water gels have been known for a very long time, the did not find any use for a long period of time because they had undesirable brittle and cohesive properties. They were, therefore, inferior to the highly elastic pectin and gelatin gels normally employed. This situation changed with the discovery, more than 30 years ago, that by incorporating a neutral polymer (in this case locust bean gum), the brittleness and stiffness of pure carrageenan gels could be modified, so as to give an elastic gel. Agar, kappa-carrageenan and xanthan also show this synergistic effect with locust bean gum. With agar, and especially with kappa-carrageenan, this manifests itself in greater gel strength and elasticity of the gels. In the case of xanthan, which by itself is not a gelling agent, locust bean gum forms thermo-reversible gels of high cohesion or very viscous solutions at extremely low concentrations.

The other galactomannans mentioned, namely guar gum and tara gum, do not show this synergistic effect, or show it only to a greatly diminished extent. This is all the more astonishing since all three of the polysaccharides mentioned belong to the group of the galactomannans and differ from one another only in respect to the different ratio of galactose:mannose. Thus, for example, in guar gum every second mannopyranose ring of the main chain bears a galactopyranose ring. This corresponds to a galactose content of 33–34% and a mannose content of 66–67%. In tara-galactomannan a galactopyranose unit is linked to only every third mannopyranose unit of the main chain. This results in a galactose:mannose ratio of 25:75.

Locust bean gum is a galactomannan having a mannose main chain in which, on the average, every fourth mannopyranose unit is substituted by a galactose residue. Although the average ratio of galactose:mannose is about 1:4, the galactose side groups are often arranged so that zones of continuous galactose substitution are formed in the mannose base structure, i.e., regions in which every mannopyranosyl unit is substituted by a galactose residue, as well as zones with relatively long sections of unsubstituted mannose base structure.

Foodstuff gels exhibit viscoelastic properties. Whether the elastic (solid) or viscous (liquid) component predominates depends on the forces which act on the rheological system and accordingly on the degree to which the cross-linked network structure is damaged. In practice, various methods of measurement and various measurements are employed to characterize the elastic properties of a gel. One can differentiate between methods of measurement in which the elastic limits of the gel are exceeded and the gel breaks, and methods of measurement in which only the elastic deformation of gels is measured, without exceeding the elasticity limits. In this latter group belong instruments such as the Bloom-Gelometer, B.A.R.-Jellytester, Exchange Ridgelimeter, F.I.R.A. Jellytester, Cox and Higby SAG method and modifications thereof, and the Saverborns cylindrical torsion method.

Within the framework of the present invention, the F.I.R.A. Jellytester was used for the gel measurements and the Brookfield RVT rotary viscometer for the viscosity measurements. The F.I.R.A. Jellytester essentially consists of a narrow metal sheet which is mounted on a shaft which bears an accurate and easily readable scale calibrated from −10 to +90 degrees of angle. This entire device can be rotated when a torsional force is acting. The torsional force is generated by running water, which runs at a predetermined rate, into a small vessel equipped with a counterweight and connected to the shaft by means of a tension device. The gel strength is measured by dipping the metal blade into the gel and allowing water to run into the small vessel until the metal blade rotates through a certain angle. The higher the amount of water required to reach the predetermined deformation angle, the greater the gel strength. In the examples below, the deformation angle is 30° and the amount of water required to produce this is quoted in ml.

According to the invention, it has now been found that a galactomannan gum obtained from the endosperm portions of *Cassia* seeds exhibits, in contrast to guar gum and tara gum, a strong synergism with the red algae extracts carrageenan and agar, as well as with the biopolymer xanthan. This synergism is moreover substantially greater than the synergism which locust bean gum shows with these polysaccharides. This effect was entirely surprising since it was previously assumed that the synergistic effect of locust bean gum occupied a special position among the galactamannans.

The subject of the present invention is therefore a gelling agent and thickener based on *Cassia*-galactomannans which contains a synergistic mixture of (a) *Cassia*-galactomannan, and (b) carrageenan, agar and/or xanthan, or consists of such a mixture.

The *Cassia*-galactomannan employed according to the invention is in particular a product originating from the botanical species *Cassia occidentalis* (Linn.), *Cassia tora* (L. Baker) or its synonyms *Cassia obtusifolia* (Linn.) and *Cassia toroides*.

The components of (a), i.e., the *Cassia*-galactomannan, and (b), i.e., the carrageenan, agar and/or xanthan, are in general present in a weight ratio of (a):(b)=(10–90):(90:10), preferably in a weight ratio of (a):(b)=(40–60):(60–40).

To improve the gel forming properties, the gelling agent and thickener according to the invention can additionally contain potassium, calcium and/or ammonium ions. The addition of electrolyte is particularly advantageous if carrageenan is present. Thus, especially if kappa-carrageenan is present, it can be advantageous to add 1%–50%, preferably 10%–40%, by weight of potassium chloride, relative to component (b). The gelling agent and thickener according to the invention can be in the form of a powder mixture and can best be handled in this form.

When heated in water, gelling occurs, and the composition can also be supplied in a partially gelled or completely gelled form, with lesser or greater water content.

The gelling agents and thickeners according to the invention can be employed advantageously in all sectors where the water-thickening action of galactomannan, carrageenan, agar-agar or xanthan is required. Examples of typical fields of use are feedstuffs (animal fodder), foodstuffs, flocculating agents, sedimentation aids and filter aids, the mining and water treatment sectors, thickeners for pharmaceutical and cosmetic purposes, additives for paper-making, additives in petroleum drilling and water drilling, explosives formulations, water-retention agents (for example in building materials), thickeners (for example in textile uses such as printing pastes, adhesives and sizes), tobacco binders, and many other fields of use where a man skilled in the art exploits the thickening, gelling, suspending, emulsifying, stabilizing, lubricating, film-forming and bonding properties of such thickeners and gelling agent systems. Feedstuff gels and foodstuff gels containing the gelling agents according to the invention often exhibit better organoleptic properties than gels which consist only of carrageenan or agar.

In the examples, parts are by weight.

EXAMPLE 1

This example demonstrates the difference in synergistic behavior between the various galactomannans of guar, tara, locust bean and *Cassia* with respect to gel formation of kappa-carageenan, 1:1 mixtures of galactomannan and commercially obtainable kappa-carrageenan (Danagel CCX) were prepared. Four parts of these gelling agent mixtures were stirred into 1,000 parts of water at room temperature, using a high-speed stirrer.

The mixture was then heated for five minutes to 85° C. in a beaker, with gentle stirring. Shortly before cooling, the water lost during heating was compensated for by adding hot water. The slightly viscous solutions were poured, while still hot, into the measuring beaker belonging to the F.I.R.A. Jellytester. After the material had cooled to 23° C. in a thermostat, the gel strengths were measured on the following day in terms of the number of ml of water required tio deflect the scale on the test instrument by 30°. This procedure was adhered to in all the investigations using the F.I.R.A. Jellytester.

| Mixture | Gel Strength |
| --- | --- |
| Guar gum/carrageenan | no gel formation |
| Tara gum/carrageenan | no gel formation |
| Locust bean gum/carrageenen | hardly any gel formation, not measurable |
| Cassia gum/carrageenan | 8 |

EXAMPLE 2

In this example, the amount of gelling agent mixtures according to Example 1 was increased from 4 parts to 6 parts/1,000 parts, since in Example 1 no measurable gel formation occurred with locust bean gum.

| Mixture | Gel Strength |
| --- | --- |
| Guar gum/carrageenan | no gel formation |
| Tara gum/carrageenan | slight gel formation, not measurable |
| Locust bean gum/carrageenan | 23 |
| Cassia gum/carrageenan | 33 |

The result shows that replacing locust bean gum galactomannan by *Cassia*-galactomannan leads to stronger gelling. In the *Cassia*/kappa-carrageenan system the gel strength is about 30% higher than in the locust bean gum/carrageenan system. The other two galactomannans, from guar and tara, gave gel formation which was either zero or below the limit of measurement with the F.I.R.A. Jellytester.

EXAMPLE 3

This example illustrates the influence of potassium ions on the gel system according to the invention. Commercially obtainable kappa-carrageenans are in the form of mixed salts and on average contain 3.5% of calcium, 0.1% of magnesium, 1.5% of potassium and 1.5% of sodium. Kappa-carrageenan does not gel in the pure sodium form. Accordingly, in practice potassium, calcium and ammonium ions are often added to intensify the gel formation. With kappa-carrageenan the strongest gels are produced by potassium ions. Typical amounts of potassium chloride added are up to 50% of the kappa-carrageenan component employed, depending on the end use. That is, in aqueous systems it is entirely customary to add up to 3 g/l of potassium chloride. 1:1 mixtures of commercially obtainable locust bean gum and kappa-carrageenan (Danagel CCX) as well as *Cassia*-galactomannan gum were prepared on the F.I.R.A. Jellytester. As in Example 1, 4 parts of gelling agent mixture were weighed out per 1,000 parts of water, which additionally contained 1 g/l of potassium chloride. In a second experiment, the amount of gelling agent mixture was increased to 6 parts/1,000 parts of water, the concentration of potassium ions being kept constant.

| Mixture | Gel Strength 4 parts/1,000 parts water | Gel Strength 6 parts/1,000 parts water |
| --- | --- | --- |
| Locust bean gum/carrageenan | 36 | 71 |
| Cassia gum/carrageenan | 44 | 80 |

This example shows clearly that the replacement of locust bean gum by *Cassia* gum still results in more than a 20% increase in gel strength when using 4 g/l of gelling agent mixture and upon addition of 0.1% of potassium chloride to the gel. When 6 g/l of gelling agent mixture are used, the advantage achieved is still more than 10%.

EXAMPLE 4

As a modification of Example 3, the concentration of potassium chloride in the gel was increased to 2 g/l, corresponding to 0.2%. In other respects, the procedure followed was as in Example 3.

| Mixture | Gel Strength 4 parts/1,000 parts water | Gel Strength 6 parts/1,000 parts water |
| --- | --- | --- |
| Locust bean gum/carrageenan | 36 | 71 |
| Cassia gum/carrageenan | 44 | 80 |

Increasing the amount of potassium chloride employed from 1 g/l to 2 g/l thus in no way changes the interrelationships presented in Example 3. When using 4 g/l of gelling agent mixture the advantage of *Cassia* gum over locust bean gum is more than 10%. When the amount of gelling agent is increased to 6 g/l, locust bean gum is still at a disadvantage of about 8% relative to *Cassia* gum.

EXAMPLE 5

In contrast to the cations mentioned in Example 3, sodium ions weaken the gel network structure and lead to lower gel strengths. Again, 1:1 mixtures of locust bean gum/carrageenan and *Cassia* gum/carrageenan were prepared and gels, which additionally contained 0.5%, 1% and 3% of sodium chloride, were prepared from these in a known manner.

| 6 parts of mixture/ 1,000 parts of water | 0.5% of NaCl | 1% of NaCl | 3% of NaCl |
| --- | --- | --- | --- |
| Locust bean gum/carrageenan | 21 | 15 | 7 |
| Cassia gum/carrageenan | 43 | 31 | 12 |

It is seen that gel-weakening electrolytes such as sodium chloride do not alter the fact (illustrated in Examples 1–4) that the behavior of the *Cassia* galactomannan gum is superior to that of the locust bean galactomannan gum.

In all three of the sodium chloride concentration ranges shown in the example, *Cassia* gum shows about 50% superiority in gel strength over locust bean gum.

EXAMPLE 6

This example describes the galactomannan/xanthan system and compares the synergistic effects of the individual galactomannans with the biopolymer xanthan.

The rheological properties are above all characterized by xanthans exhibiting extremely pseudoplastic flow characteristics without, however, actually forming gels. This means that after passing the yield point, the viscosity diminishes proportionately to the shearing stress when such stress is applied. The original viscosity becomes reestablished almost immediately after the shearing stress when such stress is applied. The original viscosity becomes reestablished almost immediately after the shearing stress has ceased. The table which follows shows the cold viscosities and hot viscosities of guar, locust bean, tara and *Cassia tora* L. galactomannan as well as of xanthan. In each case, 1% strength aqueous solutions were employed, and the measurements carried out on the Brookfield RVT viscometer at 20° C. and 20 rpm. The viscosity measurements were carried out after the polymer powder had been stirred into the water for 20 minutes, using a high speed stirring system, so as to give a lump-free solution, and the solution had been allowed to stand for a total of two hours. The hot viscosity is the viscosity measured after again stirring the polymer powder into the water for 20 minutes to give a lump-free solution, but then heating the solution for five minutes to about 90° C., topping up to replace the water lost thereby, and cooling to 20° C.

|  | Hot viscosity | Cold viscosity |
|---|---|---|
| *Cassia tora* L. | 260 mPas | too low to measure |
| Locust bean | 2,450 mPas | 78 mPas |
| Tara | 3,600 mPas | 3,040 mPas |
| Guar | 5,300 mPas | 5,100 mPas |
| Xanthan (Rhodigel 23) | 3,200 mPas | 3,200 mPas |

1:1 mixtures of galactomannan and xanthan were then prepared, stirred into water at 1% strength, heated to 90° C. and cooled to 20° after topping up to replace the water lost.

The guar gum/xanthan mixture showed no gel formation and the tara gum/xanthan mixture minimum gel formation. The most powerful gelling properties were shown by the system *Cassia tora* L. gum/xanthan. The results are shown in the table.

| Mixture | Gel Strength |
|---|---|
| Guar gum/xanthan | no gel formation |
| Tara gum/xanthan | 2 |
| Locust bean gum/xanthan | 4 |
| *Cassia tora* L. gum/xanthan | 11 |

The gel strengths were again measured on the F.I.R.A. Jellytester and the angle of deflection was 30°, as in all the other preceding cases.

What is claimed is:

1. A method for gelling or thickening a solution comprising adding an effective amount to said solution of a synergistic mixture of (a) 10–90 parts by weight of *Cassia-tora* galactomannan and (b) 90–10 parts by weight of carrageenan, agar, xanthan or mixtures thereof as the gelling or thickening agent.

2. The method of claim 1 wherein said mixture comprises 40–60 parts by weight of (a) and 60–40 parts by weight of (b).

3. In a foodstuff or feedstuff which contains a gelling or thickening agent, the improvement comprising using as the gelling or thickening agent a synergistic mixture of (a) 10–90 parts by weight of *Cassia*-tora galactomannan and (b) 90–10 parts by weight of carrageenan, agar, xanthan or mixtures thereof.

4. The foodstuff or feedstuff of claim 3 wherein the mixture comprises 40–60 parts by weight of (a) and 60–40 parts by weight of (b).

5. The method of claim 1 wherein said mixture further comprises potassium ions, calcium ions, ammonium ions or mixtures thereof.

6. The method of claim 2 wherein said mixture further comprises potassium ions, calcium ions, ammonium ions or mixtures thereof.

7. The method of claim 5 wherein said mixture comprises 1%–50% by weight of potassium chloride, relative to the weight of component (b).

8. The method of claim 7 wherein said mixture comprises 10%–40% by weight of potassium chloride, relative to the weight of component (b).

9. The method of claim 6 wherein said mixture comprises 1%–50% by weight of potassium chloride, relative to the weight of component (b).

10. The method of claim 9 wherein said mixture comprises 10%–40% by weight of potassium chloride, relative to the weight of component (b).

11. The foodstuff or feedstuff of claim 3 wherein said mixture further comprises potassium ions, calcium ions, ammonium ions or mixtures thereof.

12. The foodstuff or feedstuff of claim 4 wherein said mixture further comprises potassium ions, calcium ions, ammonium ions or mixtures thereof.

13. The foodstuff or feedstuff of claim 11 wherein said mixture comprises 1%–50% by weight of potassium chloride, relative to the weight of component (b).

14. The foodstuff or feedstuff of claim 13 wherein said mixture comprises 10%–40% by weight of potassium chloride, relative to the weight of component (b).

15. The foodstuff or feedstuff of claim 12 wherein said mixture comprises 1%–50% by weight of potassium chloride, relative to the weight of component (b).

16. The foodstuff or feedstuff of claim 15 wherein said mixture comprises 10%–40% by weight of potassium chloride, relative to the weight of component (b).

* * * * *